(12) United States Patent
Fullman

(10) Patent No.: US 7,993,316 B1
(45) Date of Patent: Aug. 9, 2011

(54) SANITARY DEVICE AND METHOD

(76) Inventor: Jack V. Fullman, Hopatcong, NJ (US)

( * ) Notice: Subject to any disclaimer, the term of this patent is extended or adjusted under 35 U.S.C. 154(b) by 865 days.

(21) Appl. No.: 11/903,997

(22) Filed: Sep. 25, 2007

Related U.S. Application Data

(63) Continuation-in-part of application No. 10/920,141, filed on Aug. 18, 2004, now abandoned.

(51) Int. Cl.
*A61F 13/15* (2006.01)
*A61F 5/44* (2006.01)

(52) U.S. Cl. .............. 604/349; 604/351; 604/385.01; 604/346; 604/347; 604/385.11; 604/385.201

(58) Field of Classification Search ............ 604/349, 604/351, 356, 346, 347, 385.09, 385.11, 604/385.201, 385.01
See application file for complete search history.

(56) References Cited

U.S. PATENT DOCUMENTS 6,540,729 B1 * 4/2003 Wada et al. ............ 604/349
2006/0149196 A1 * 7/2006 Bjornberg et al. ........ 604/349

* cited by examiner

*Primary Examiner* — Jacqueline F Stephens

(57) ABSTRACT

A sanitary device having an absorbent pad with a pocket on one end and on the other end an opening with a pair of petals extending outward therefrom. By holding and marginally squeezing the pocket, the pocket will open and the petals will separate. A penis can be inserted into the pocket using the petals a converging guide. Penile excretions can the be absorbed in the absorbent pad before discarding it. Further embodiments include absorbent pads fabricated from feminine pads and alternative closure elements.

32 Claims, 9 Drawing Sheets

SANITARY DEVICE AND METHOD

This is a Continuation-In-Part of U.S. patent application Ser. No. 10/920,141, filed 18 Aug. 2004 now abandoned.

FIELD OF THE INVENTION

The present invention relates to sanitary devices and methods, and in particular to devices and methods for absorbing penile excretions.

BACKGROUND OF THE INVENTION

A significant percentage of the male population have a urine stream that is affected by an enlarged prostate or by some other medical condition or recent medical or surgical procedure. The affected urine stream may be slow and may end so gradually that small amounts of urine may trickle or drip from the penis after the individual has ostensibly finished urinating. Consequently, an individual, even when careful, may spot his clothing with urine before or after closing his pants. This type of problem also occurs with the trickling or dripping of semen after ejaculation. Beside excretion of urine or semen, other excretions can occur in connection with various surgical procedures for pathologies.

SUMMARY OF THE INVENTION

In accordance with the illustrative embodiments demonstrating features and advantages of the present invention, there is provided a sanitary device for absorbing penile excretions. The sanitary device has an absorbent pad with a pocket on one end and on the other end a pair of petals. The petals can separate to provide separate guides for guiding a penis into the pocket.

In accordance with another aspect of the invention a method is provided for absorbing penile excretions with an absorbent pad having a pocket on one end and on the other end a pair of petals. The method includes the step of holding and marginally squeezing the pocket to open the pocket and separate the petals. Another step is inserting a penis into the pocket using the petals as a converging guide. The method also includes the step of absorbing penile excretions in the absorbent pad and discarding it.

Devices and methods of the foregoing type are highly effective in capturing penile excretions. In some embodiments the absorbent pad comprises an absorbent inner layer covered with a non-absorbent outer layer. The pad can be two separate opposing sections that are joined together along a portion of their margins. Alternatively, the pad can be formed from a longer strip that is folded and then sealed along a portion of the margin of the two folded sections.

In either case, the device will have a pocket that may be sealed at least partially along three sides, together with a pair of petals extending from the pocket. In one embodiment the petals are arranged so that when the pocket is squeezed along its margins and opens, the petals spread to form two converging sides for guiding the insertion of the penis into the pocket.

In some embodiments the margins of the absorbent pad can be secured together by glue, adhesive tape, stitches, crimping, plastic rivets, staples, etc. In other embodiments an opposing pair of absorbent layers can be covered with wider non-absorbent layers that are then attached together by heat sealing or gluing to form a pocket.

In still other embodiments, the absorbent pad may be tethered to an undergarment with a clothing clip. That feature allows the pad to remain in place to continue absorbing for an extended time or to provide convenient storage for a future single use or repetitive use.

BRIEF DESCRIPTION OF THE DRAWINGS

The above brief description as well as other objects, features and advantages of the present invention will be more fully appreciated by reference to the following detailed description of presently preferred but nonetheless illustrative embodiments in accordance with the present invention when taken in conjunction with the accompanying drawings, wherein.

DETAILED DESCRIPTION OF THE EXEMPLARY EMBODIMENTS

Figure 1:
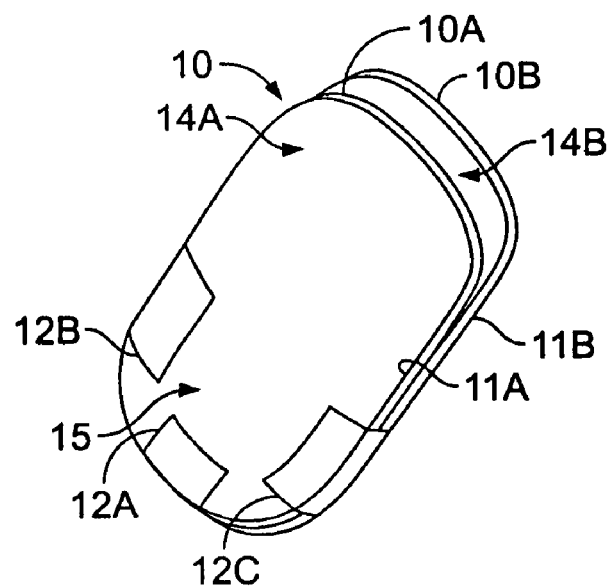
FIG. 1 is perspective view of a sanitary device in accordance with principles of present invention.
Figure 2:
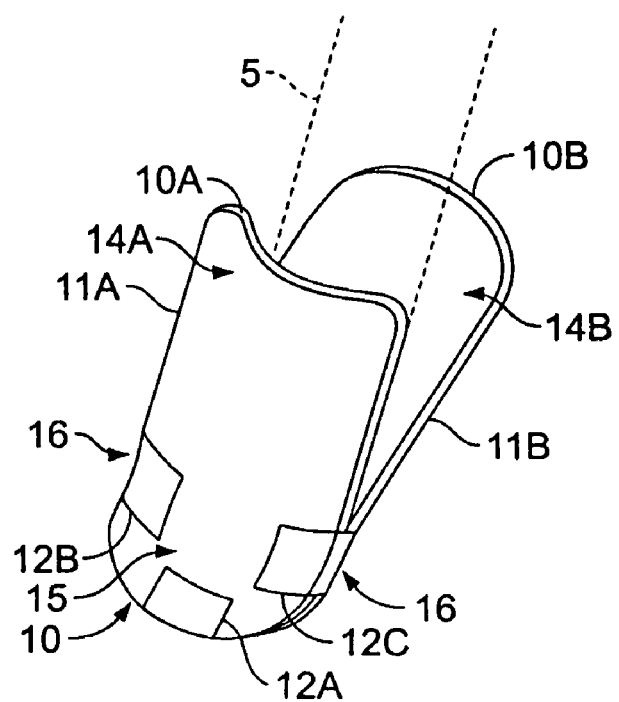
FIG. 2 is perspective view of the device of FIG. 1 shown being squeezed along its margins to open the illustrated petals.
Figure 3:
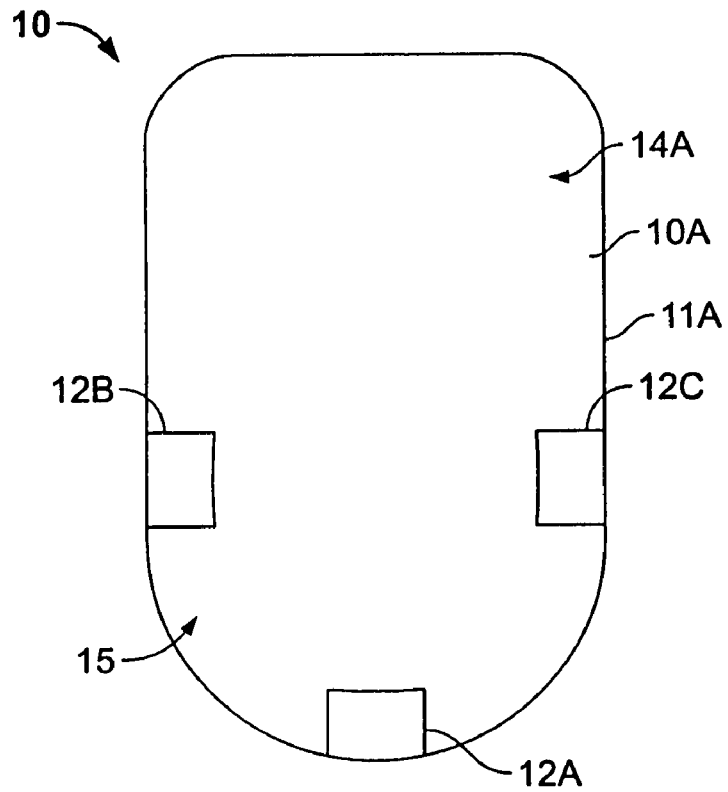
FIG. 3 is a front view of the device of FIG. 1.

Referring to FIGS. 1-3, the illustrated sanitary device is shown as a an absorbent pad 10 having opposing sections 10A and 10B in the form of a pair of swaths joined along portions of their margins 11A and 11B to form a pocket 15. Pocket 15 has rounded corners and is closed along a marginal seam by three sections of adhesive tape; namely, bottom tape section 12A and side tape sections 12B and 12C.

In other embodiments tape sections 12B and 12C may be a single band of adhesive tape that encircles the top of pocket 15. It will be appreciated that in some embodiments a single strip of adhesive tape may be run edgewise along a portion of the margins 11A and 11B to form a pocket that is fully closed on three sides, that is, closed on the right, left, and bottom. Instead of adhesive tape, a marginal seam can be made by directly gluing margins 11A and 11B, or by stitching, crimping, stapling, riveting, etc.

Extending from the top of pocket 15 are a pair of petals 14A and 14B, which are integral parts of pads 10A and 10B. As shown in FIG. 2, finger pressure applied along the margins 11A and 11B at positions 16 will tend to open pocket 15 and spread petals 14A and 14B, which can then act as penile insertion guides in a manner to be described presently. Petals 14A and 14B are shown with rounded outer edges, but in this embodiment the rounding is less than the rounding associated with the bottom of pocket 15, which is essentially semicircular.

The absorbent pads 10A and 10B may be made of various absorbent materials such as paper-like products, synthetic foam layers, layers made of the fibers often found in cloth, thread, and yarn, layers containing hydrophilic fibers or substances, etc. In some embodiments it will be desirable to impregnate the pads 10A and 10B with fragrances or antibacterial agents. Also, in some embodiments these pads may be similar to the pads used in sanitary napkins currently available for absorbing menses from females, both human and non-human. For example, the pads used for menstruating dogs and cats is relatively thin (about ⅛ inch, or 3.2 mm) but is found to have sufficient absorbing capacity for the purposes intended herein.

In this embodiment, the illustrated sanitary device has an overall length of three inches (7.6 cm) and a width of two inches (5.0 cm), although different dimensions and proportions can be employed in alternative embodiments. Moreover, while the overall outline is rectangular, some embodiments may have an outline that is circular, oval, elliptical, triangular, polygonal, etc. The length of the pocket 15 (the depth of pocket 15 as measured along the length of the sanitary device) is in this embodiment 40% of the overall length, but may be a different percentage in other embodiments. Advantages flow from having the pocket length less than half the overall length (namely, increasing the initial opening and enhancing the guiding properties of the petals), although some embodiments will have the pocket approximately half the overall length or longer.

Figure 4:
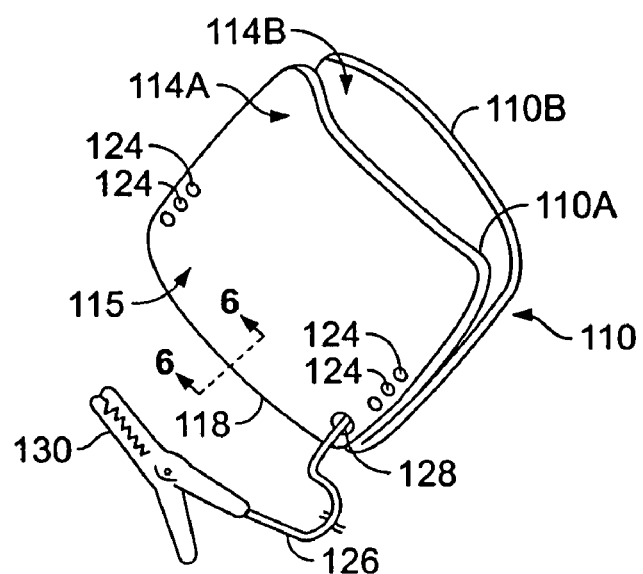
FIG. 4 is perspective view of a tethered sanitary device that is an alternate to that of FIG. 1.
Figure 5:
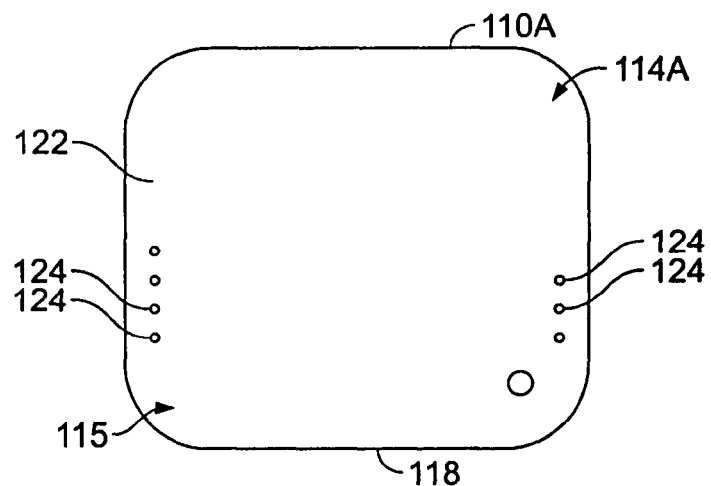
FIG. 5 is a front view of the device of FIG. 4.
Figure 6:
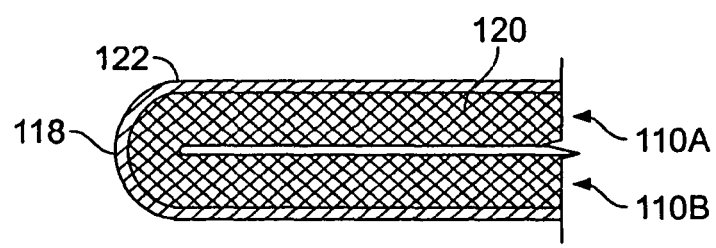
FIG. 6 is a detailed, fragmentary, cross-sectional view of the bottom of the pocket taken along line 6-6 of FIG. 4.

Referring to the alternative embodiment of FIGS. 4-6, components corresponding to those previously illustrated have the same reference numerals but increased by 100. The sanitary device of FIGS. 4-6 is about three inches (7.6 cm) wide and two inches (5.0 cm) long (the longitudinal dimension being defined as the direction into the depth of the pocket 115).

It will be noted that the pad sections 110A and 110B are one integral piece that merge at the fold 118. Also, the pad material is shown formed with an absorbent inner layer 120 and an optional non-absorbent outer layer 122. Non-absorbent layer 122 may be a flexible, thin plastic, flesh-colored sheet that is adhesively secured or crimped to absorbent layer 120. Pocket 115 is therefore closed on the bottom by the fold 118. Pocket 115 is also closed on the sides by a number of plastic rivets 124.

A tether 126 made of string or elastic cord, is attached to a hole 128 in a lower corner of pocket 115. The tether 126 can be secured by a knot (not shown) on the proximal end of the tether, or otherwise. The distal end of tether 126 is attached to a clothes clip 130, shown as an alligator clip.

Figure 7:
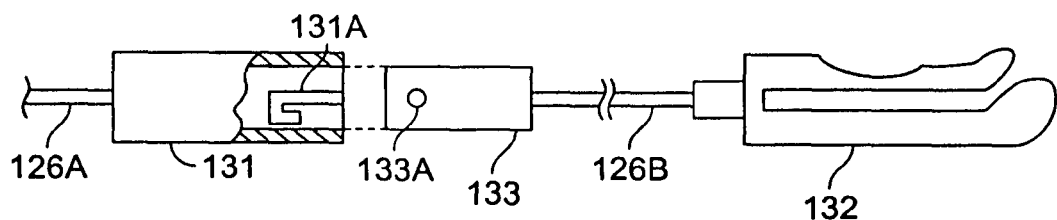
FIG. 7 is a side view of a clothing clip that is an alternate to that shown in FIG. 4.

Referring to FIG. 7, the previously mentioned alligator clip (clip 130) is replaced with a simple clip 132 having no moving parts. In this embodiment the previously mentioned tether (tether 126) has been replaced by two tether segments 126A and 126B. These two segments 126A and 126B are separately connected to socket 138 and plug 133, respectively. Socket 131 is a plastic cylinder having an open-end that carries a hooked groove 131A that is sized to receive cylindrical stub 133A on the side of plug 133 to form a quick-disconnect fastener. Plug 133 can be inserted into sleeve 131 so that stub 133A slides toward the end of groove 131A before being twisted a quarter turn to bring stub 131A to the hooked end of groove 131A. It will be appreciated that in some embodiments stub 133A and groove 133A may be provided in diametrically oppose pairs to balance the forces and increase the fastening strength.

This arrangement allows the user to keep the clip 132 and plug 133 indefinitely while discarding socket 131 and the sanitary device that is attached thereto through tether 126A.

Figure 8:
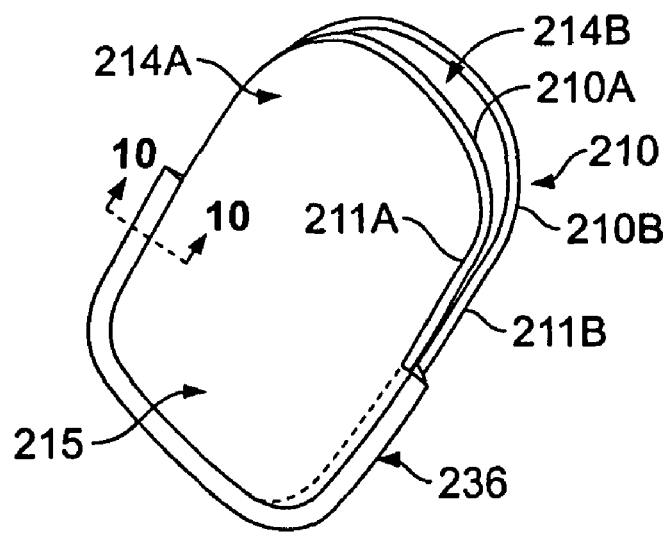
FIG. 8 is perspective view of a sanitary device that is an alternate to that shown in FIGS. 1 and 4.
Figure 9:
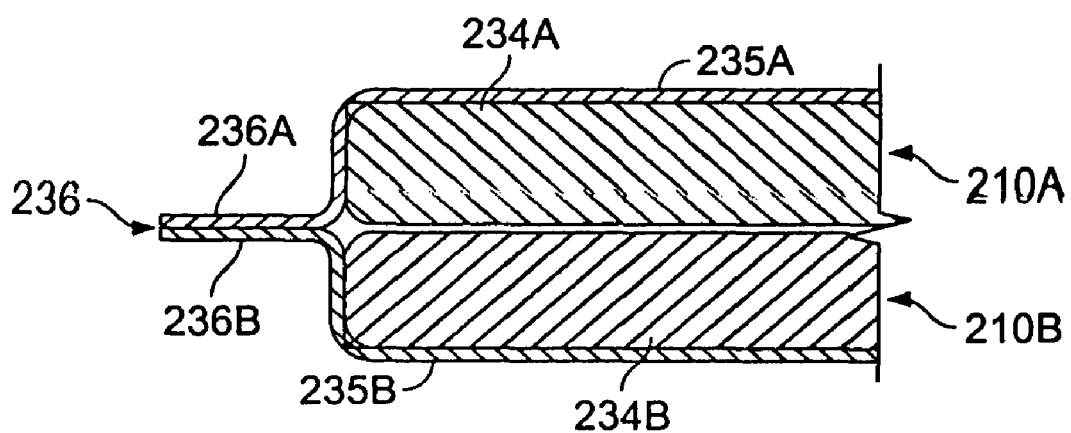
FIG. 9 is a detailed, fragmentary, cross-sectional view of the edge of the pocket taken along line 10-10 of FIG. 8.

Referring to FIGS. 8 and 9, components of the illustrated sanitary device that are similar to components of the embodiment of FIG. 1 have the same reference numerals but increased by 200. Here, absorbent pads 210A and 210B have absorbent inner layers 234A and 234B, respectively, which layers are covered by non-absorbent outer layers 235A and 235B. These outer layers 235A and 235B may be thin plastic sheets secured to layers 234A and 234B.

In the petal regions 214A and 214B the outer layers 235A and 235B have the same outline as the inner layers 234A and 234B, but extend beyond them in the pocket region 215 to form a marginal seam 236. The seam 236 is composed of edging portions 236A and 236B which are secured together by adhesives, heat sealing, crimping, or other means. The seam 236 provides a U-shaped marginal seam extending along the bottom and part of the sides of pocket 215. In other embodiments the bottom seam may be formed otherwise or may be provided by a fold between integral sections of absorbent pads, in which case an edging portion can still be employed but need only provide an opposing pair of seams.

Figure 10:
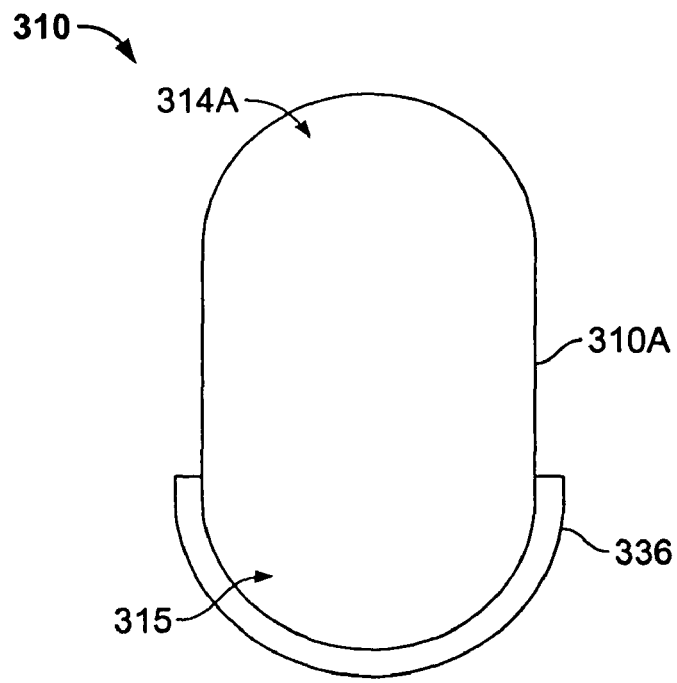
FIG. 10 is a front view of a sanitary device that is an alternate to that shown in FIG. 8.

In this embodiment the outer edge of petals 214A and 214B are rounded into a semicircular profile. The bottom of pocket 215 is not semicircular but has rounded corners. The sanitary device 310 of FIG. 10 is almost the same as the embodiment of FIG. 8 except that both the bottom of pocket 315 and the outer edges of the petals (petal 314A of pad 310A illustrated only) are semicircular in outline.

Figure 11:
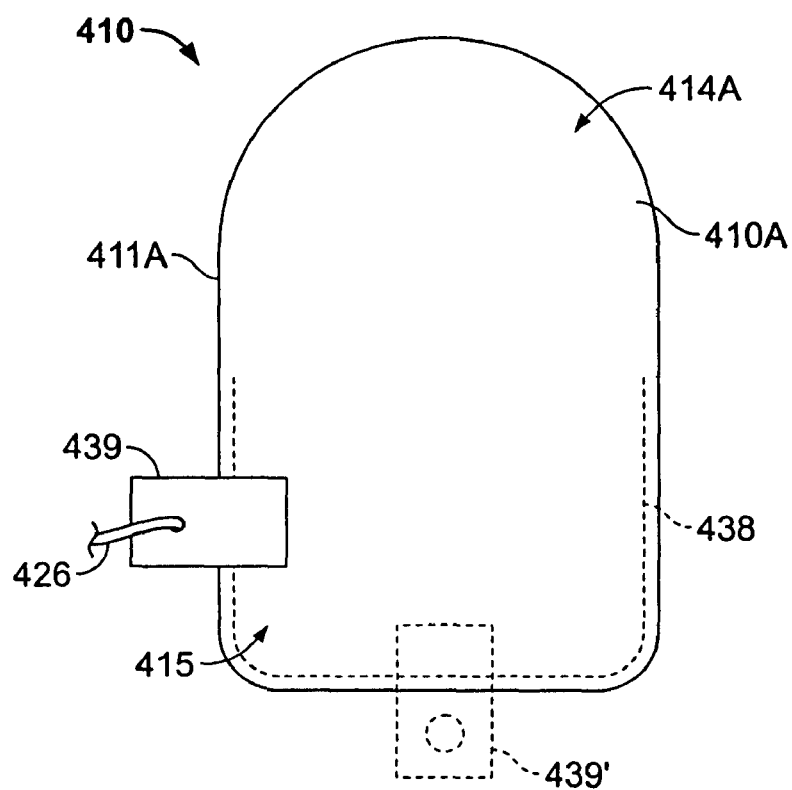
FIG. 11 is a front view of a sanitary device that is an alternate to those previously illustrated.

The sanitary device 410 of FIG. 11 is almost the same as the embodiment of FIG. 3 except that the bottom of pocket 415 has rounded corners (i.e., not a semicircular outline) while the outer edges of the petals (petal 414A of pad 410A illustrated only) are semicircular in outline. In addition, pocket 415 is formed by stitches 438 that run in a U-shaped pattern along the edge of the pads (only edge 411A of pad 410A being illustrated). It will also be noted that the pocket 415 has a length that exceeds the length of the petals (e.g., petal 414A).

Additionally, tag 439 is formed from adhesive tape that is folded in half, portions of each half being attached to the device 410 along a side edge (specifically overlapping the edge 411A in this embodiment). Alternatively, a tag 439', shown in phantom, can be attached to a bottom edge of device 410. In this embodiment device 410 has an overall length of 2⅞ inches (7.3 cm) and an overall width of two inches (5.1 cm).

Figure 12:
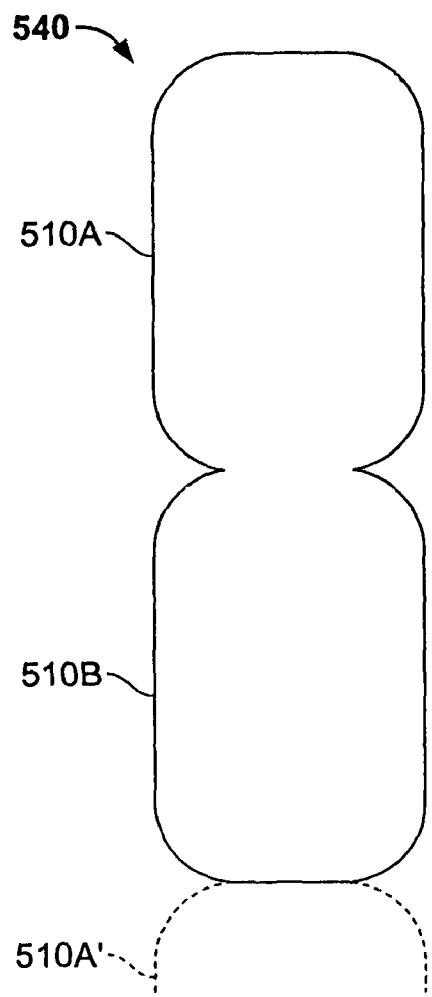
FIG. 12 is a plan view of a strip that can be formed into a sanitary device similar to those previously illustrated.

Referring to FIG. 12, a strip 540 is shown having a repeating pattern. Specifically, a pair of absorbent pads 510A and 510B constitute one cycle of the repeat. The beginning of the next cycle is shown as absorbent pad section 510A'. It is anticipated that strip 540 will be part of a larger web that is slit longitudinally to form many strips before the strips are run through a rotary die to form the illustrated outline. Strip 540 will also be severed between repeats either by the rotary die or at a separate severing station. A subsequent station can automatically fold the two sections 510A and 510B and seal their margins in a manner similar to that described above to form the pockets and petals of the type previously described.

In other embodiments sections 510A and 510B may be identical. In such embodiments the two identical sections can be severed and then secured together in a manner similar to that described in connection with FIG. 1, 10, or 11. In some cases, a non-absorbent layer will be secured to the absorbent pads after these pads have been attached together to form a pocket. Instances are also anticipated where a non-absorbent layer can be applied by spraying or by rolling the pads over rollers wetted with the fast drying substance. In some cases, separate strips may be formed and then brought together to overlay one another. Thereafter, portions of the edges of the strip may be periodically connected to form the sides of a pocket, while contemporaneously severing and sealing discrete intervals of the strip to form the bottom of a pocket.

Figure 13:
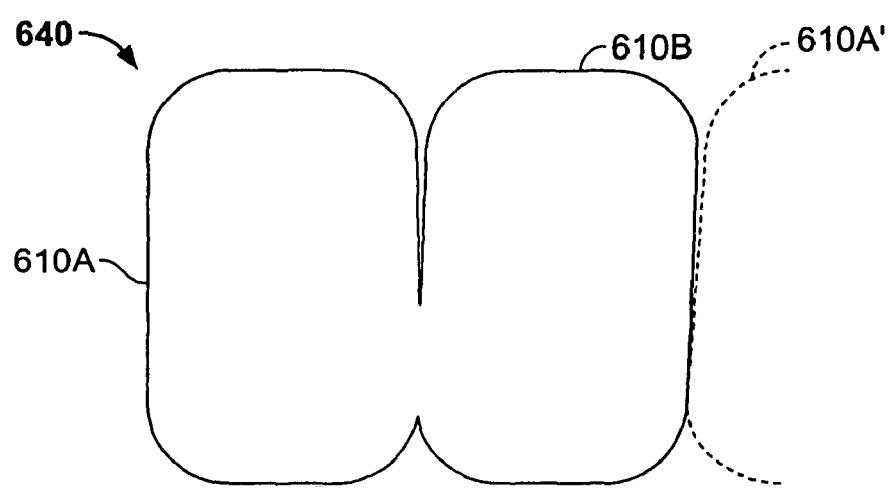
FIG. 13 is a plan view-of another strip that can be formed into a sanitary device similar to those previously illustrated.
Figure 14:
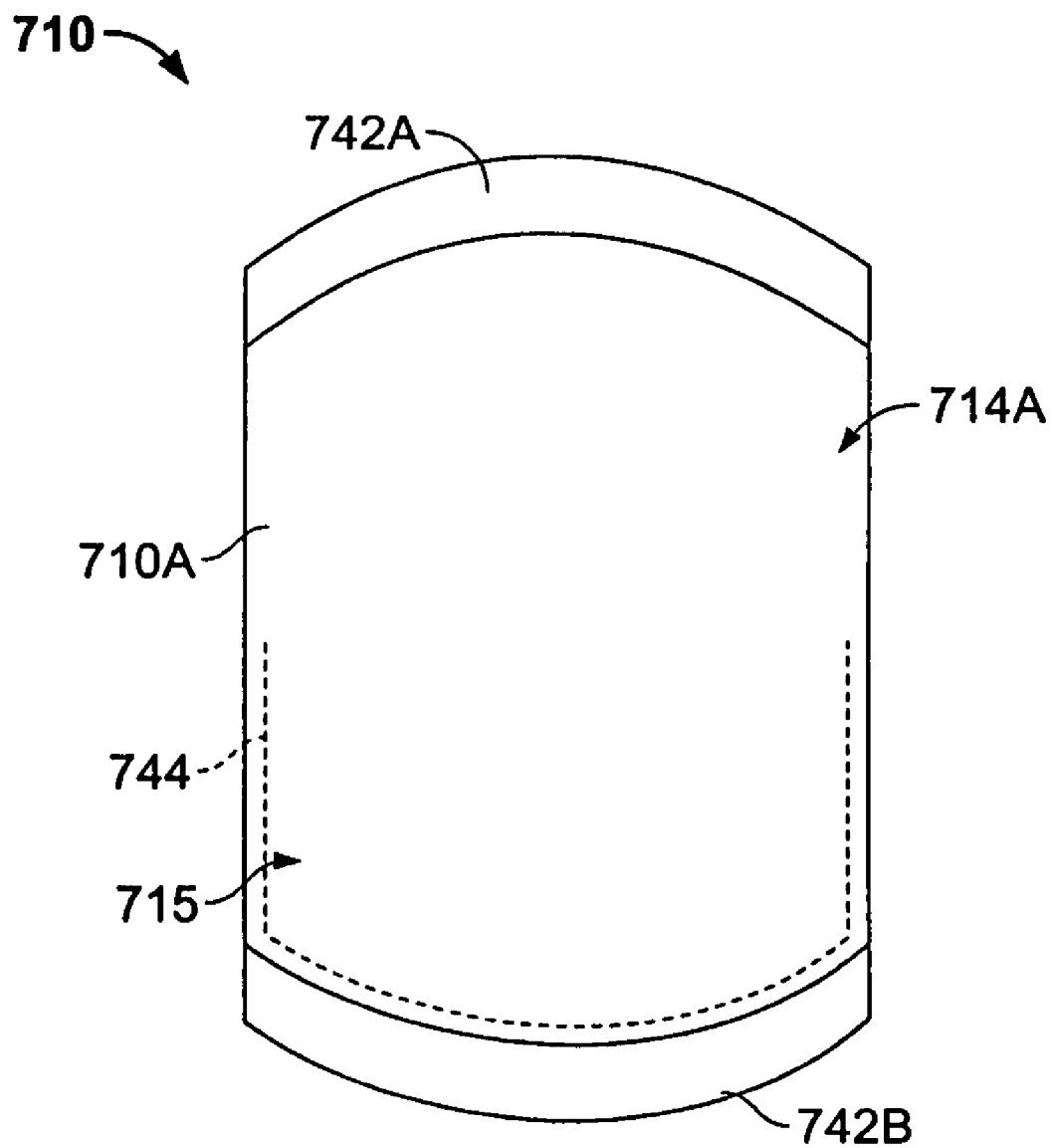
FIG. 14 is a plan view of a further embodiment.

Referring to FIG. 13, another strip 640 is very similar to that previously described in connection with FIG. 12 except that the repeat (sections 610A and 610B) are connected side-by-side. Sections 610A and 610B can be severed as a pair and folded to form a marginal seam on one side before the other side and the bottom are sealed to form of pocket of the type previously described. Again, sections 610A and 610B may be identical and can be severed and placed together to form the sanitary device similar to that shown in FIG. 1. Referring to the alternative embodiment of FIG. 14, components corresponding to those previously illustrated in FIG. 1 have the same reference numerals but increased by 700. The sanitary device of FIG. 14 is about three inches (7.6 cm) long and two inches (5.0 cm) wide.

It will be noted that a pair of separate, overlaying pad sections (only pad section 710A visible in this view) are glued together along U-shaped glue line 744. 410 Also, similar to the embodiment of FIG. 8, the pad material is formed with an absorbent inner layer a non-absorbent outer layer that are crimped together along opposite borders 742A and 742B to form the pocket 715.

To facilitate an understanding of the principles associated with the foregoing apparatus, its operation will be briefly described in connection with the embodiment of FIGS. 1-3. The sanitary device 10 may be supplied in individually wrapped packages or in a package containing a number of the sanitary devices. Since device 10 is relatively thin (e.g. ¼ inch) one or more of them can be conveniently carried in a pocket or wallet.

After urinating (or ejaculating) the user can shake the penis to expel, to the extent possible, excretions remaining in the urethra. The user can then fetch device 10 and pinch it at positions 16 to open pocket 15 and simultaneously spread the petals 14A and 14B. Petals 14A and 14B can spread a variable amount so that device 10 is a single size that can fit all users. Also, the spreading of petals 14A and 14B provides a relatively large opening that can easily accept and guide the shaft of the penis S toward pocket 15. Since in one embodiment the petals 14A and 14B are themselves absorbent they can immediately begin catching any dripping or dribbling penile excretions. At the same time, the fingers are located at a distant location 16 and will therefore remain dry.

Once the head of the penis is lodged in pocket 15 pressure can be released from locations 16. The pads 10A and 10B are somewhat springy and will therefore spring back around penis S to gently clamp device 10 in place. In this position, penile excretions will continue to be absorbed by the pads 10A and 10B. In fact, the absorbency of the pads 10A and 10B will perform a wicking action that tends to remove the remaining penile excretions in the urethra. The user can keep the sanitary device 10 in position for a period of time that seems appropriate as a matter of judgment or experience. Some users may feel comfortable leaving the sanitary device 10 on the penis S for an extended period of time after closing the pants, but such extended wear will be unnecessary in most instances. In most instances the user will remove the sanitary device 10, close his pants, and discard device 10.

An advantage of devices of the type just described are their relatively small size. Thus, a user standing at a urinal can discreetly place the device 10 in position while it remains shielded by the user's palm and not visible to casual observers. Likewise, the small size of device 10 enables the user to discreetly carry the device 10 in a closed hand out of view, before using or discarding the device. The unobtrusive nature of device 10 is also enhanced when it has a flesh-colored plastic covering.

For the device of FIG. 4 a user may use clip 132 to clip the device 110 to an undergarment well before there is in need to use the device. In that case device 110 will be conveniently located for immediate use without the need to prepare by fetching the device, removing a wrapper, etc. Also, clip 132 can be used to keep device 110 secured inside the pants after use. This may be helpful where the user does not wish to immediately carry device 110 to a disposal container. This delayed disposal may either be a simple preference or may be prompted by a desire to use device 110 again, which may be important for individuals with a chronic condition involving frequent urination.

Figure 15:
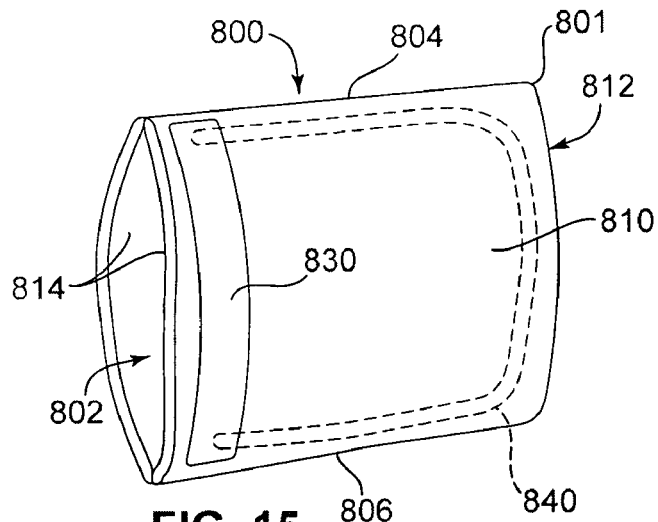
FIG. 15 is a perspective view of a further embodiment according to the present invention.
Figure 17:
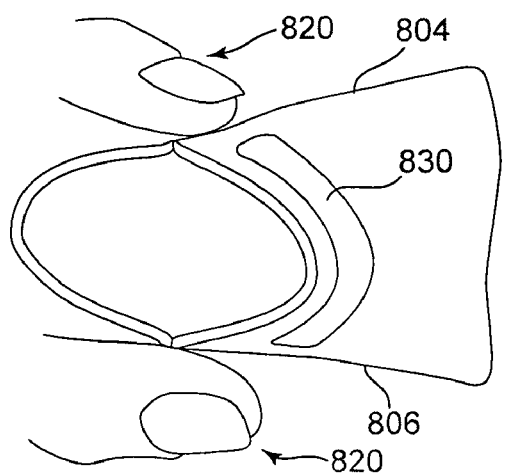
FIG. 17 is a perspective view of the compression applied to the opening of the various embodiments.

A further embodiment 800 is shown in FIG. 15 comprising an open-ended envelope sized to receive the member therein through an opening 802 on one side and having closed edges 804 and 806 sized to retain the desired member girth and length therein. Typically, the envelope 801 is generally rectangular having a dimension of 3 inches in length by 2½ inches across the opening 800 and both may be enlarged or for other applications reduced. Moreover, alternate embodiments may provide one or more of edges 804, 806, 808 as curved or other style, together or separately. The embodiment 800 shown in FIG. 15 comprises an outer surface 810 folded at 812 and having an inner absorbent material 814 attached thereto, and the edges 804 and 806 are formed by connection of the outer surface by glue, weld, tape, etc. which effective reduces or eliminates a thickness contribution at the edge seam due to the inner material 814. When the constituent material of the outer surface 810 has at least a minimal resilience toward a substantially planar form, the thickness contributed by the inner material 814 inward from the edges 804, 806 and optionally the fold 812 biases opposing outer surfaces 810 to bow outward in the middle (distal from the edges 804, 806) when compression force 820 is applied across the outer edges 804, 806 as shown in FIG. 17, and return to a closed disposition when such compression force is removed.

Alternate embodiments include a resilient strip 830 applied to at least on of the outer surfaces 810 proximal to the opening 802 which similarly responds to compression force 820, and returns the opening 802 to a closed position when relaxed in the absence of the compression force 820. A spring member 840 may also be used to provide a force to close the opening 802, yet yield when a compression force 820 is applied.

Figure 16:
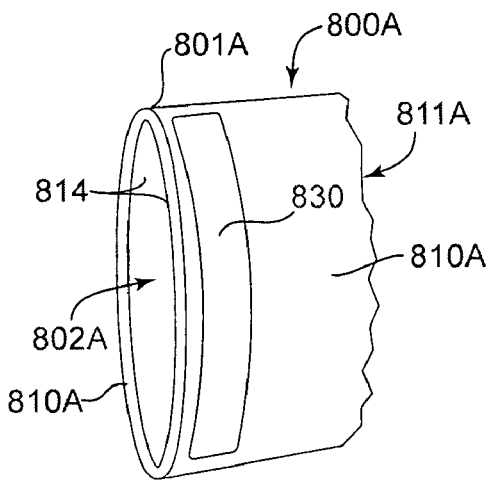
FIG. 16 is a perspective view of variant of the embodiment of FIG. 14.

Further alternate embodiment 800A shown in FIG. 16 comprising a substantially tubular member 811A having a substantially continuous outer surface 810A around the circumference of the opening 802A and substantially continuous inner absorbent surface 814A, including a resilient strip 830 or spring member 840 (FIG. 14) attached thereto or inserted therein. When relaxed (without compression applied) the resilient strip 830 and/or the spring member 840 urges the outer surface 810A (and the retained absorbent lining 814) into a flattened disposition into a flattened disposition. When compression is applied (as shown in FIG. 17), a more rounded opening (wider transverse to the plane of the flattened disposition) to accept a user's body member therein.

Figure 18:
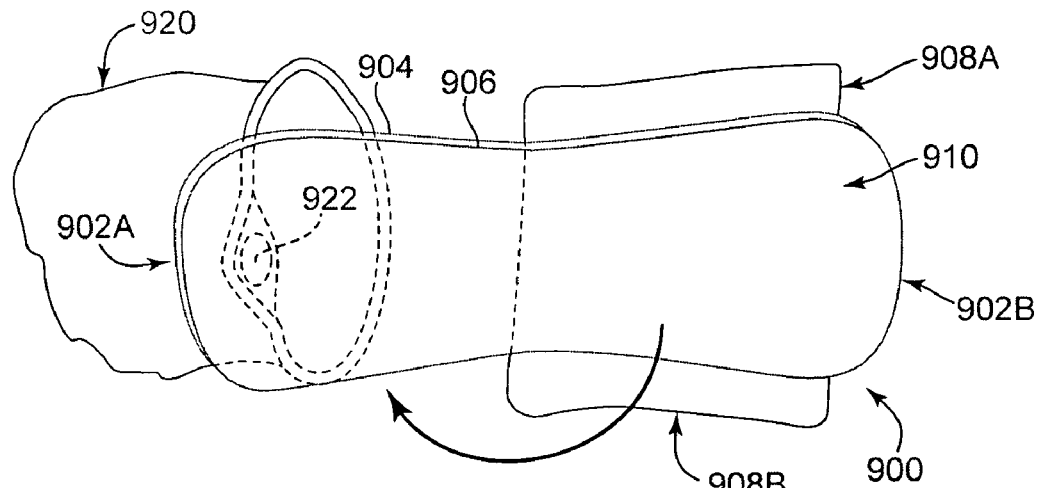
FIG. 18 is a perspective view of a further embodiment according to the present invention.
Figure 19:
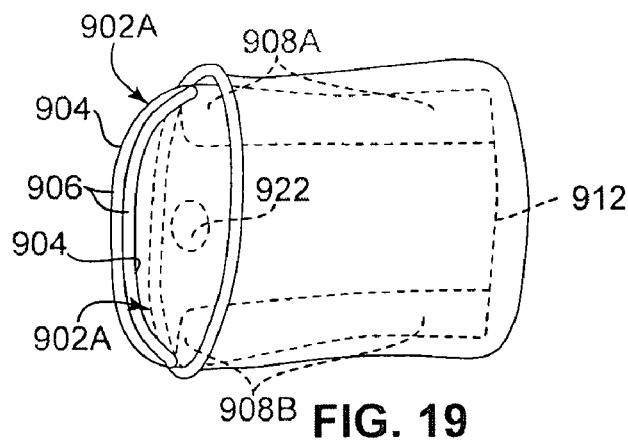
FIG. 19 is a perspective view of the embodiment of FIG. 17 adapted for male usage.

A further novel embodiment 900 according to the present invention is shown in FIGS. 18 and 19, which comprises a sanitary device usable by women, and optionally by men. An elongated planar pad 910 comprising an outer layer 904 and an absorbent layer 906 overlaying said outer layer and disposed to confront and contact the user of the sanitary device 900. Connected to or part of the outer layer are attachment members 908A and 908B, which typically comprises tape or an adhesive disposed on a surface on the same side as the absorbent layer 906, and may be covered prior to application with a material (not shown) having a surface which permits removal from the adhesive without dislocating the adhesive from the attachment member capable of forming a liquid-tight seal to the outer layer 904. A similar adhesive may optimally be applied to surface(s) of the attachment member 908A and 908B away from the absorbent layer 906 to permit securing to undergarments when used the sanitary device is used as a sanitary device for females.

When used as a sanitary device for men, the elongated planar pad 910 is folded, preferably to align and substantially overlap the ends 902A and 902B when folded. The attachment members, each generally connected to or extending from substantially one (same or different) half portion of the elongated planar pad 910, are folded over to engage the outer surface of the other portion of the folded elongated planar pad 910. If retaining adhesive thereon, the adhesive protection material (if present) is removed and the adhesive retains each attachment member 908A and 908B to the outer surface of the other portion of the folded elongated planar pad. Alternately, a separate adhesive or other form of retaining device may be applied over both portions of the folded elongated planar pad 910. When compression force is applied to the region joining the two portions of the folded elongated absorbent pad 910 by adhesive, tape, or other structures, an opening is formed between the ends 902A and 902B of the two portions of the folded elongated absorbent pad 910 to receive a body member therein, with a maximum spacing midway between the joining regions. Optionally, the ends 902A and 9026 extend outward away from the fold 912 from the joining regions to form lips or "tulips" which serve to guide and/or enhance the application of the sanitary device.

An alternate embodiment includes a flexible covering 920 which is retained to the outer covering 904 by glue, fused section, tape, etc. 922 for convenience, and optimally comprises a material connection which permits detachment without injury to the outer surface 904 if the flexible covering 920 is separated from the outer surface 904. When the elongated planar pad 910 is folded a shown in FIG. 18, the flexible covering 920 is applied over the folded elongated planar member 920 by deformation of either or both the flexible covering 920 and the folded elongated planar member 910, and provide a reserve capacity to retain fluids introduce into the folded elongated planar member 910 in the event of incomplete seal of the attachment members 908A or 908B or failure of the outer layer 904. In an alternate embodiment, the outer layer of the elongated planar member 920 or attachment members or devices which join the two portion of the folded elongated planar member 901 are not water impermeable such as the various elements mentioned above or applied by one of ordinary skill, the flexible covering 920 forms the primary fluid retention element.

Figure 20:
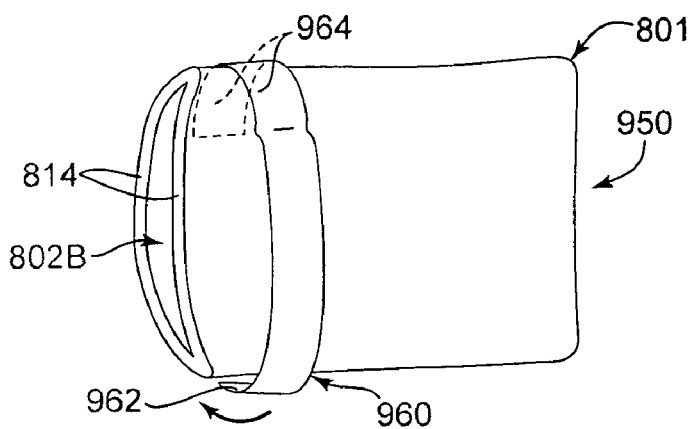
FIG. 20 is a perspective view of a further embodiment of the present invention.

A further alternate embodiment is provided in FIG. 20, wherein a pouch, such as 801 (or others, above) providing a volume and having lining 814 therein and an opening 802B with a circumferential dimension near the opening 802B further includes a restricting band 960 connected (at 964) to the pouch 801 near the opening and typically has adhesive (or equivalent) on the other, free end 962 on the side facing and selectively engaging the pouch 801. The restricting band circumscribes the pouch near the opening 802B and further selectively limits or reduces the circumferential dimension by the user affixing the free end 962 to the pouch 801 proximal to the opening 802B to grip a member inserted into the opening 802B. The restricting band 960 may be a minor (e.g. less than ½) portion of the circumferential dimension, up to or greater than the circumferential dimension (before application of the restricting band).

These and further embodiments, modifications, and substitutions according to one of ordinary skill in the art are within the scope of the present invention, which is not to be limited except by the claims which follow.

What is claimed is:

1. A sanitary device for absorbing penile excretions, comprising:
   an absorbent pad having a pocket on one end and on the other end a pair of confronting petal guides each comprising a substantially planar deformable member, wherein
   each deformable member includes a perimeter including a middle region therealong, a first and a second substantially oppositely disposed regions contiguous to said middle region and terminating in ends at said pocket, wherein each said deformable member's said middle region, said first and said second substantially oppositely disposed regions are entirely separate from the other deformable said member's said middle region, said first and said second substantially oppositely disposed regions except where they terminate at said pocket, forming completely separable petals,
   each said ends together with said perimeter defines a petal area therebetween, said petal area being contiguous to said pocket, and wherein
   each deformable member is disposed to allow movement together of said substantially oppositely disposed adjacent regions with said oppositely disposed regions of one deformable member in proximity to corresponding confronting oppositely disposed adjacent regions of the other deformable member, urging said middle region to separate from a corresponding middle region of the other said deformable member of said other petal guide to provide separate guides for guiding a penis past said perimeter into the pocket.

2. A sanitary device according to claim 1 wherein said petals are at least half as long as said pocket.

3. A sanitary device according to claim 1 wherein said petals are at least as long as said pocket.

4. A sanitary device according to claim 1 wherein said petals are longer than said pocket.

5. A sanitary device according to claim 1 wherein said pad is a folded strip with two marginal seams.

6. A sanitary device according to claim 1 wherein said pad comprises:
   a pair of swaths having margins that are partially joined.

7. A sanitary device according to claim 1 wherein said pad includes a pair of opposing sections, each comprising:
   an absorbent inner layer; and
   a non-absorbent outer cover overlaying said absorbent inner layer.

8. A sanitary device according to claim 7 wherein said outer layer of each of the opposing sections has an edging portion extending beyond said absorbent inner layer, the edging portions of each of the opposing sections being joined together.

9. A sanitary device according to claim 8 wherein the edging portions of each of the opposing sections are joined together to form a U-shaped seam.

10. A sanitary device according to claim 8 wherein the edging portions of each of the opposing sections are joined together to form an opposing pair of seams.

11. A sanitary device according to claim 7 wherein said petals terminate in a rounded edge.

12. A sanitary device according to claim 7 wherein said pocket has opposite said petals a bottom end with rounded corners.

13. A sanitary device according to claim 12 wherein said petals terminate in a rounded edge.

14. A sanitary device according to claim 1 comprising: a tether attached to said pad.

15. A sanitary device according to claim 14 comprising: a clothing clip attached distally to said tether.

16. A sanitary device according to claim 15 wherein said tether has a distal section attached to set clothing clip and a proximal section attached to said pad, the device comprising:
a quick-disconnect fastener releasably connecting the distal and the proximal sections of the tether together.

17. A method for absorbing penile excretions employing an absorbent pad having a pocket therein the method comprising the steps of:
holding and marginally squeezing the pocket to open the pocket and a pair of confronting petals each having an area of material extending from and contiguous to said open pocket at a connecting end and a terminal end distal from said open pocket and distal therefrom, said marginal squeezing of said pocket operates to separate at least a portion of the petals distal from said pocket;
guiding a penis first between said terminal end of said distal portion of said separated petals toward said pocket; and
inserting said penis into the pocket after passing said terminal end.

18. The method according to claim 17 further including the step of absorbing penile excretions by absorbing one of urine and semen.

19. A method according to claim 18 further including the step of absorbing penile excretions with a disposable absorbent pad.

20. A method according to claim 17 comprising the step of: tethering the absorbent pad to a garment.

21. A sanitary device for absorbing penile excretions, comprising:
an absorbent pad having a pocket on one end and on the other end a pair of petals that are entirely separable except where they both connect to said pocket to provide separate guides for guiding a penis into the pocket, said petals being at least as long as said pocket and terminating in a rounded edge, said pocket having opposite said petals a bottom end with rounded corners, said absorbent pad having a pair of opposing sections each including:
an absorbent inner layer; and
a non-absorbent outer cover overlaying said absorbent inner layer and having at least a minimal resilience toward a substantially planar form, said outer cover of each of the opposing sections having an edging portion extending beyond said absorbent inner layer, the edging portions of each of the opposing sections being joined together and wherein said petals are disposed relative to said opposing sections to move relatively apart when a compression force is applied to opposite edging portions of said opposing sections and return to a closed disposition when said compression force is removed.

22. A unitary sanitary device, comprising:
a pouch comprising a tubular member having a closing end and an open end; and
a resilient member combined with said pouch, having an uncompressed state disposed to urge said open end into a substantially elongated, narrow opening in corresponding first and second dimensions by extension of said resilient member, wherein said tubular member adjacent to said elongated, narrow opening form confronting portions in relative proximity according to said resilient member, and wherein compression of said resilient member forms a relatively diminished first and relatively broadened second axis opening dimensions, wherein said resilient member comprises an internal spring member having at least a portion thereof disposed perpendicular to said opening first and second dimensions.

23. The unitary sanitary device of claim 22, further including a plurality of lips connected to and extending outward from said pouch opening wherein said plurality of lips are completely separable one from another except where said plurality of lips are connected to said pouch opening.

24. A convertible sanitary napkin, comprising:
a substantially planar member elongated along a length dimensions and having a substantially parallel edges along said length and absorbent material layer on at least a portion of one side thereof and adaptable to be folded substantially perpendicular to said length to present said first and a second portion of said planar member in confronting disposition, further comprising retaining means disposed to retain said first and said second planar member portions in confronting disposition.

25. The convertible sanitary napkin of claim 24, wherein said retaining means comprises at least one extension disposed from a corresponding said edge and adapted to engage a portion of said confronting planar member portion when folded.

26. The convertible sanitary napkin of claim 25, wherein said extension includes at least one of adhesive, glue, stitching, staples and rivets for connection to said portion of said confronting planar member.

27. The convertible sanitary napkin of claim 25, wherein said extension is welded to said portion of said confronting planar member.

28. The convertible sanitary napkin of claim 25, further includes a glove attached thereto.

29. The convertible sanitary napkin of claim 28, wherein said glove is removably attached to said sanitary napkin to permit discarding thereof without damage to said napkin.

30. The convertible sanitary napkin of claim 29, wherein said glove comprises a resilient glove.

31. The convertible sanitary napkin of claim 24, further includes lips attached to, and extending from confronting ends of said planar member.

32. A unitary sanitary device, comprising:
a pouch including an absorbent lining and having a perimeter enclosing a volume and including an opening in said perimeter to provide access into said volume, said pouch further having an outer circumferential dimension proximal said opening;
a restricting band having one end connected to said pouch proximal said opening and an opposite, free end having means for engaging said pouch thereon, said restricting band disposed to selectively circumscribe at least a portion of said pouch proximal said opening to selectively diminish said circumferential opening.

* * * * *